United States Patent
Chang et al.

(10) Patent No.: US 8,092,387 B2
(45) Date of Patent: Jan. 10, 2012

(54) ULTRASONIC IMAGING TECHNIQUE FOR DIFFERENTIATING THE DISTRIBUTION OF SCATTERERS WITHIN A TISSUE

(75) Inventors: Chien-Cheng Chang, Taipei (TW); Po-Hsiang Tsui, Taipei (TW); Chien-Chung Chang, Taipei (TW); Chin-Chou Chu, Taipei (TW); Jen-Jen Lin, Taipei (TW)

(73) Assignee: National Taiwan University, Taipei (TW)

( * ) Notice: Subject to any disclaimer, the term of this patent is extended or adjusted under 35 U.S.C. 154(b) by 1184 days.

(21) Appl. No.: 11/826,082

(22) Filed: Jul. 12, 2007

(65) Prior Publication Data

US 2008/0114242 A1    May 15, 2008

(30) Foreign Application Priority Data

Nov. 10, 2006    (TW) .............................. 95141676 A

(51) Int. Cl.
*A61B 8/00*    (2006.01)
(52) U.S. Cl. ........................ 600/443; 600/437
(58) Field of Classification Search .................. 600/437, 600/443
See application file for complete search history.

(56) References Cited

OTHER PUBLICATIONS

Wang et al., "A Feasibility Study on the Development of Ultrasonic Parametric Imaging Based on Nakagami Statistical Model", IEEE Ultrasonics Symposium, vol. 3, pp. 2133-2136, 2004.*
Shankar, "A General Statistical Model for Ultrasonic Backscattering from Tissues", IEEE Transactions on Ultrasonics, Ferroelectrics, and Frequency Control, vol. 47, No. 3, May 2000.*
Shankar et al., "Classification of Ultrasonic B-Mode Images of Breast Masses Using Nakagami Distribution", IEEE Transactions on Ultrasonics, Ferroelectrics, and Frequency Control, vol. 48, No. 2, Mar. 2001.*
Dumane et al., "Use of Frequency Diversity and Nakagami Statistics in Ultrasonic Tissue Characterization", IEEE Transactions on Ultrasonics, Ferroelectrics, and Frequency Control, vol. 48, No. 5, Sep. 2001.*
Shankar, "Ultrasonic Tissue Characterization Using a Generalized Nakagami Model", IEEE Transactions on Ultrasonics, Ferroelectrics, and Frequency Control, vol. 48, No. 6, Nov. 2001.*
Shankar, "A Compound Scattering pdf for the Ultrasonic Echo Envelope and Its Relationship to K and Nakagami Distributions", IEEE Transactions on Ultrasonics, Ferroelectrics, and Frequency Control, vol. 50, No. 3, Mar. 2003.*
Tsui et al., "A feasibility study on the determination of blood hematocrit with Nakagami parameter calculated backscattered signals", IEEE Ultrasonics Symposium, vol. 3, pp. 1683-1686, 2005.*

* cited by examiner

*Primary Examiner* — Brian Casler
*Assistant Examiner* — Jonathan Cwern
(74) *Attorney, Agent, or Firm* — Bacon & Thomas, PLLC

(57) ABSTRACT

An ultrasonic imaging technique for differentiating the distribution of scatterers within a tissue comprises a correcting and an imaging procedure. The correcting procedure includes steps of obtaining ultrasonic backscattered signals from a standard phantom, compensating and demodulating the signals into an envelope image, calculating the parameter m and $\overline{m}$, selecting a window to calculate parameter $m_w$ in each location of the envelope image and $\overline{m}_w$, if $\overline{m}_w \neq \overline{m}$ then increase the size of the window to repeat the steps above, and when $\overline{m}_w = \overline{m}$, it is the optimal size of the window. The imaging procedure includes steps of obtaining ultrasonic backscattered signals from a target tissue, compensating and demodulating the signals into an envelope image, calculating $m_w$ in each location to form a $m_w$ matrix, and presenting the matrix by utilizing pseudocolors.

2 Claims, 13 Drawing Sheets

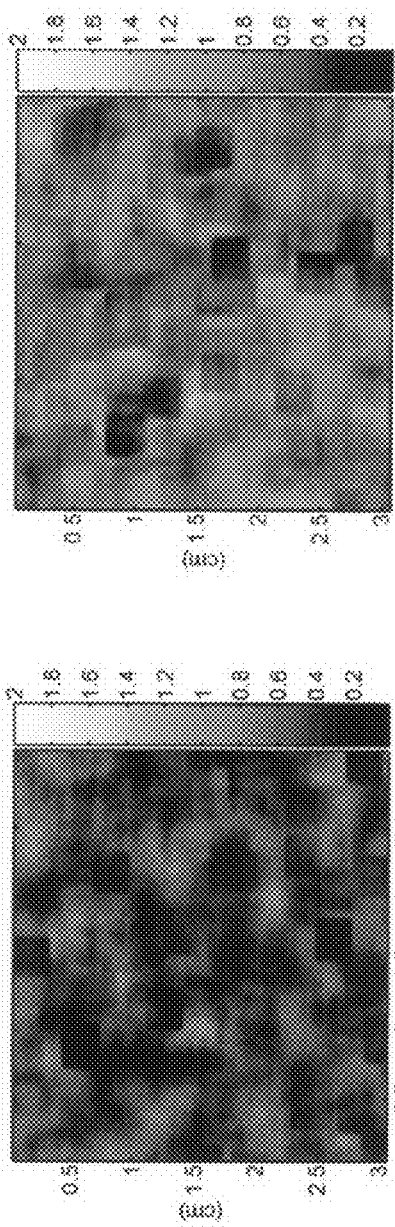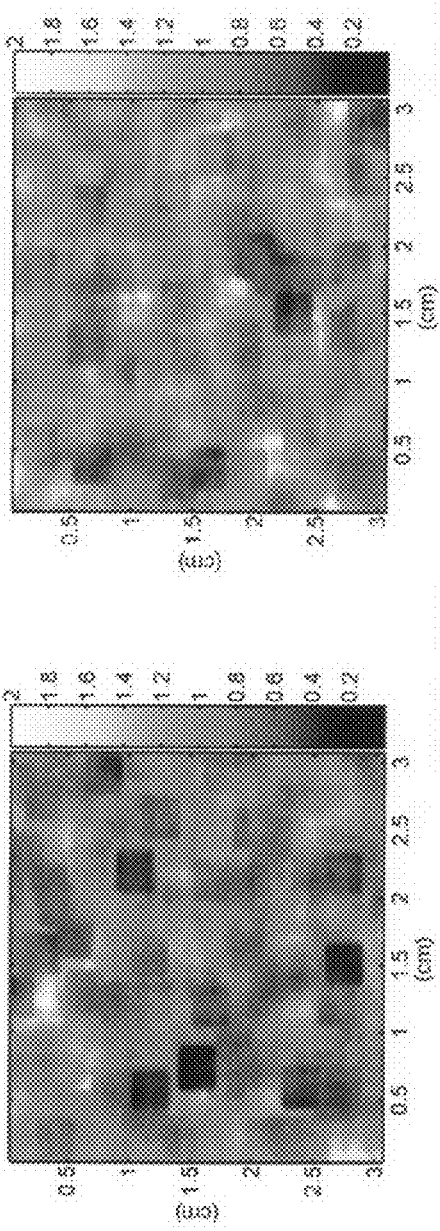

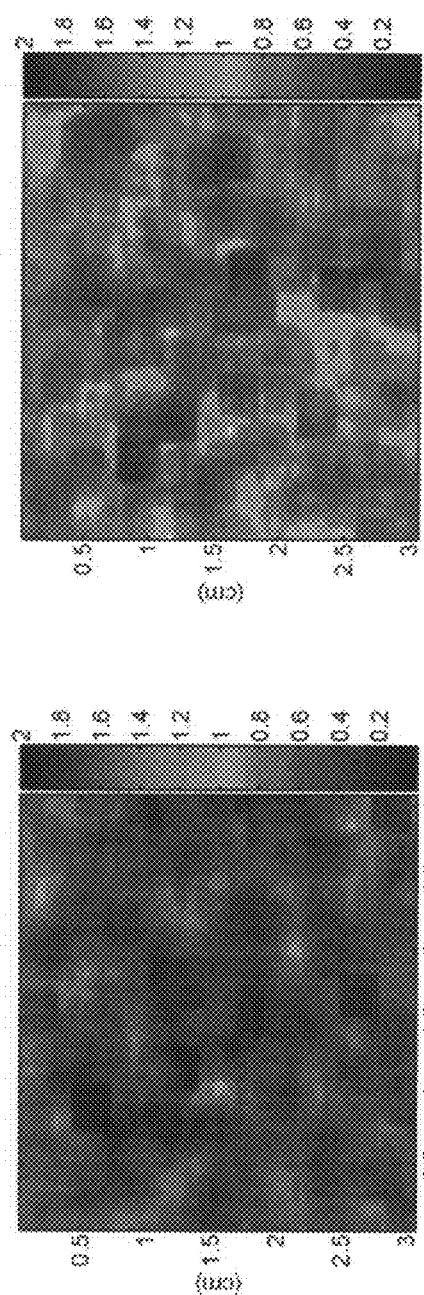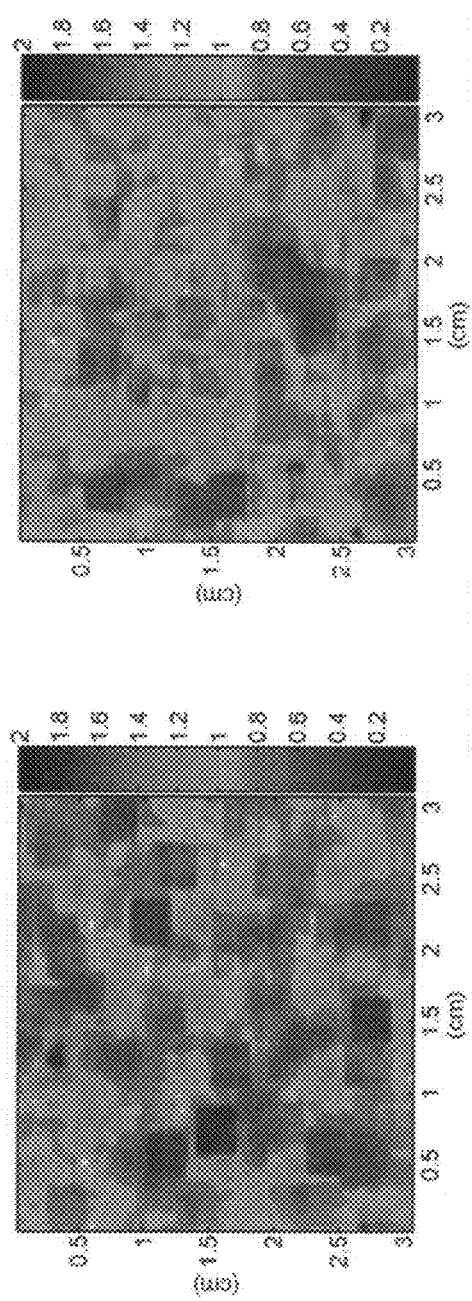
FIG. 8A  FIG. 8B  FIG. 8C  FIG. 8D

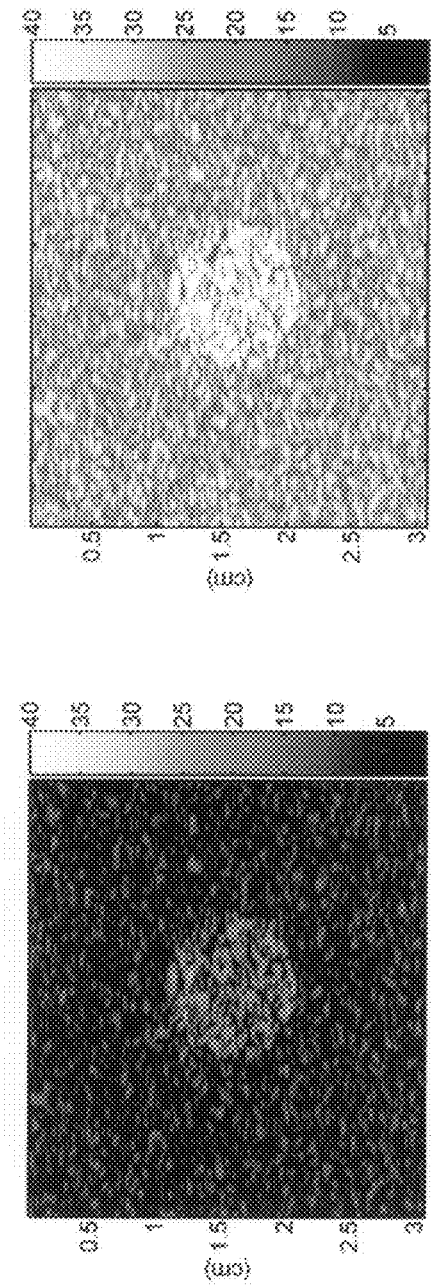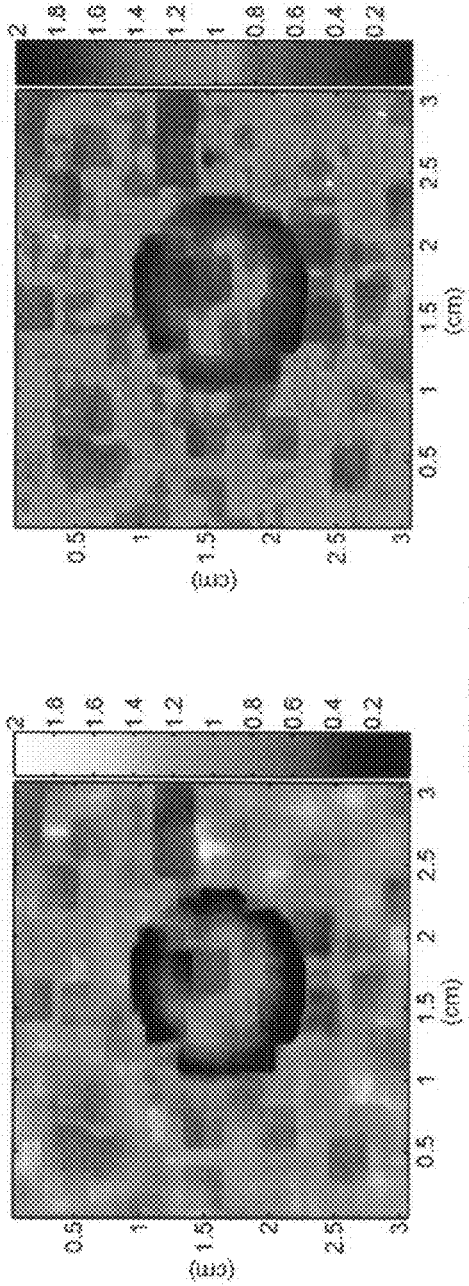
FIG. 10A  FIG. 10B  FIG. 10C  FIG. 10D

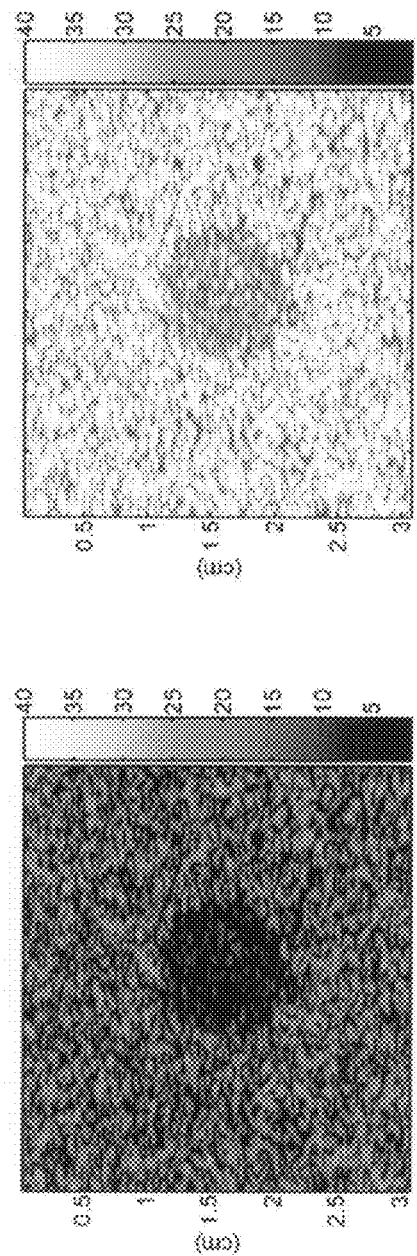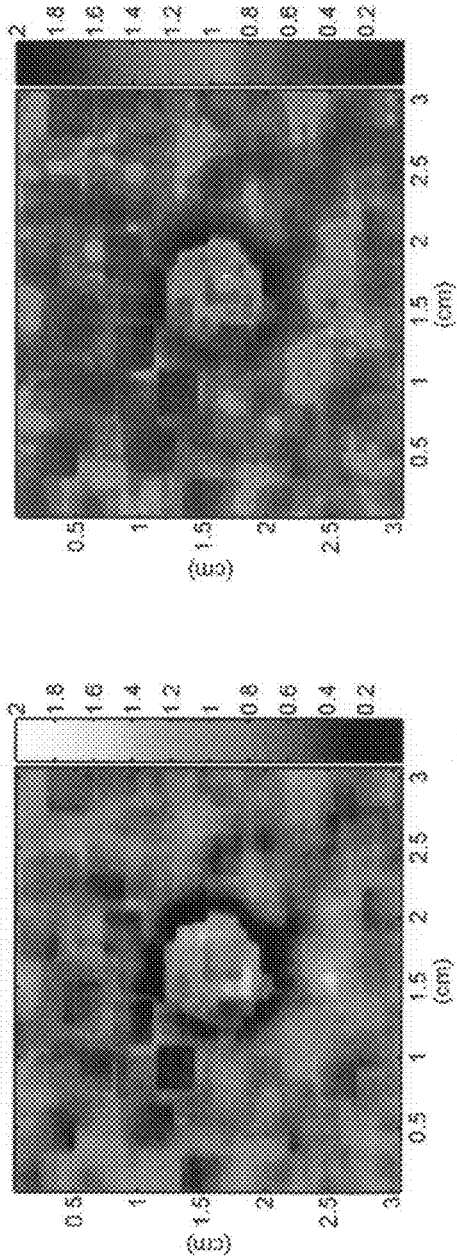
FIG. 11A  FIG. 11B  FIG. 11C  FIG. 11D

ULTRASONIC IMAGING TECHNIQUE FOR DIFFERENTIATING THE DISTRIBUTION OF SCATTERERS WITHIN A TISSUE

CROSS REFERENCE TO RELATED APPLICATIONS

This application claims priority to Taiwan application 095141676.

BACKGROUND OF THE INVENTION

1. Field of the Invention

The present invention relates to an ultrasonic imaging technique for differentiating the distribution of scatterers within a tissue, especially to an ultrasonic imaging technique for differentiating the distribution of scatterers within a tissue, which utilize Nakagami parameter m and has a correcting and an imaging procedure.

2. Description of the Prior Art

The grayscale ultrasound image system (B-mode) is a frequently used tool to noninvasively examine the tissue anatomy in the medical diagnosis. The grayscales in the B-mode image are determined according to the strengths of the echoes from the changes in acoustic impedance in the tissues. However, the use of the B-mode image in the clinical diagnosis might suffer from some disadvantages.

First, to more clearly visualize the structures in a tissue, the typical ultrasonic scanner allows operators to adjust different system parameters, such as the system gain, time-gain compensation (TGC), and dynamic range. Moreover, different ultrasonic scanners made by different manufacturers have different procedures of signal and image processing. It means that the B-mode image is easily affected by the system factors.

Second, the specular reflection is highly angle-dependent. When the sound beam is perpendicular to the interface of the tissue, the transducer can receive a large amount of the returned acoustic energy. Otherwise, only less energy is received. It implies that the brightness of the B-mode image also rely on the skill and training of the operators.

Third, during imaging, the scattering will occur when the incident wavelength is greater or comparable to the dimension of the scatterers in a tissue. The generated backscattered signals would form the so-called speckle, which often exhibits a granular pattern of white and dark spots in the ultrasonic B-mode image.

To avoid the influence of the speckle effect on the image quality, many methods were proposed to reduce the speckle appearance in the B-mode image. Nevertheless, due to that the backscattered signals are actually dependent on the shape, size, density, and other properties of the scatterers in a tissue, the information related to the scatterers carried by both the backscattered echoes and other weak signals might be lost in the B-mode image.

To resolve the dilemmas of the ultrasonic B-scans, different kinds of quantitative methods that are independent of the effects from the systems and operators are developed to provide the information of the scatterers, which may be associated with the nature of the biological tissues, for assisting in the diagnosis of the B-mode image. Considering the randomness of the ultrasonic backscattered signals, many researchers apply various statistical distributions to model the shape of the probability density function (pdf) of the backscattered echoes for the tissue characterization. The Rayleigh distribution is the first model used to describe the statistics of the ultrasonic backscattered signals. The pdf of the backscattered envelope would follow the Rayleigh distribution when the resolution cell of the ultrasonic transducer contains a large number of randomly distributed scatterers. It should be noted that the scatterers in most biological tissues have various possibilities of arrangements. If the resolution cell contains the scatterers that have randomly varying scattering cross sections with a comparatively high degree of variance, the envelope statistics are the pre-Rayleigh distributions. If the resolution cell contains the periodically located scatterers in addition to the randomly distributed scatterers, the envelope statistics are the post-Rayleigh distributions. And therefore some useful distributions including Rician, K, homodyned K, and generalized K are applied to encompass both the pre-Rayleigh and post-Rayleigh statistics of the backscattered envelope. However, the computational complexity of these models in their parameter estimations may limit their practical applications.

Several years ago, the Nakagami distribution, initially proposed to describe the statistics of the radar echoes, was applied to the statistical analysis of the ultrasonic backscattered signals. The Nakagami statistical model has comparatively less computational complexity and is general enough to describe a wide range of the scattering conditions in medical ultrasound, including pre-Rayleigh, Rayleigh, and post-Rayleigh distributions. Although the Nakagami distribution can fit well with the pdf of the ultrasonic envelope, a compounding statistical distribution may be more appropriate to model the envelope statistics, because the ultrasonic signals returned from the tissues may contain contributions from more than one mechanism. Hence, the compounding Nakagami distributions involving the Nakagami-Gamma, Nakagami-lognormal, and Nakagami-inverse Gaussian were subsequently developed to fit more closely to the envelope statistics of the ultrasonic backscattered echoes from tissues. In these distributions, the primary parameter to determine the backscattered statistics is the Nakagami parameter, which is estimated from the statistical moments of the ultrasonic backscattered envelope. It only depends on the shape of the backscattered envelope and has been demonstrated using computer simulations and experiments on phantoms to have a good ability to differentiate different scatterer concentrations in a medium. The Nakagami parameter has also been applied to practical measurements on biological tissues to classify the scatterer properties, such as the bone, skin, breast, and blood.

As a result of the outstanding ability of the Nakagami parameter to detect the variation of the scatterer concentration, this parameter was suggested to form the parametric image in making a medicine diagnosis, and afterward some preliminary studies and applications have been performed. However, there is no complete report related to the Nakagami parametric image to date.

SUMMARY OF THE INVENTION

The primary object of the present invention is to provide an ultrasonic imaging technique for differentiating the distribution of scatterers within a tissue, which will not be affected by system settings and user operations.

Another object of the present invention is to provide an ultrasonic imaging technique for differentiating the distribution of scatterers within a tissue for evaluating the concentration and arrangement of scatterers in a biological tissue.

Still another object of the present invention is to provide an ultrasonic imaging technique for differentiating the distribution of scatterers within a tissue for assisting the use of a B-mode ultrasonic image.

To achieve the above objects, the present invention provides an ultrasonic imaging technique for differentiating the distribution of scatterers within a tissue by utilizing Nakagami parameter m, comprising a correcting and a imaging procedure, wherein:

the correcting procedure comprises steps of:
a. obtaining ultrasonic backscattered signals from a standard phantom in which a large amount of scatterers are randomly distributed and have the same size and acoustic impedance;
b. compensating for the effect of attenuation, divergence, and noise for each signal;
c. demodulating each signal to form an envelope image of the phantom;
d. calculating the parameter m of each envelope in the envelope image and the mean value $\overline{m}$;
e. selecting a window whose length and width are respectively equal to the pulselength, moving the window a pixel at a time across the envelope image from its left-top where is the beginning site; calculating the value of the parameter $m_w$ whenever the window is moved to a new location until the window is completely through the envelope image; and calculating the mean value $\overline{m}_w$; and
f. determining whether the value $\overline{m}_w$ is equal to the mean value $\overline{m}$, if not, then increasing the length and width of the window and repeating the step e; and if $\overline{m}_w = \overline{m}$, the window has its optimal size; and the imaging procedure comprises steps of:
g. obtaining ultrasonic backscattered signals from a biological tissue
h. compensating for the effect of attenuation, divergence, and noise for each signal;
i. demodulating each signal to form an envelope image of the biological tissue;
j. forming a parameter m matrix corresponding to the biological tissue by utilizing the window of optimal size obtained in step f to calculate the value $m_w$ of each location of the envelope image; and
k. generating an image that displays the parameter m matrix in step j by utilizing pseudocolors.

The following detailed description, given by way of examples and not intended to limit the invention solely to the embodiments described herein, will best be understood in conjunction with the accompanying drawings.

BRIEF DESCRIPTION OF THE DRAWINGS

FIGS. 4A and 4B show the conventional B-mode image and its grayscale histogram for the type-I phantom of the scatterer concentration of 8 scatterers/mm$^2$, wherein FIG. 4A is with constant system gain and different dynamic ranges and FIG. 4B is with constant dynamic range and different system gains.

FIGS. 5A and 5B show the conventional B-mode image and its grayscale histogram for the type-I phantom of the scatterer concentration of 16 scatterers/mm$^2$, wherein FIG. 5A is with constant system gain and different dynamic ranges and FIG. 5B is with constant dynamic range and different system gains.

FIG. 7A-7D show Nakagami parametric images according to the present invention with a grayscale display for the type-I phantoms of various scatterer concentrations, wherein FIG. 7A is with 2 scatterers/mm$^2$, FIG. 7B is with 4 scatterers/mm$^2$, FIG. 7C is with 8 scatterers/mm$^2$, and FIG. 7D is with 16 scatterers/mm$^2$.

FIG. 8A-8D show the Nakagami parametric images according to the present invention with a pseudocolor display for the type-I phantoms of various scatterer concentrations, wherein FIG. 7A is with 2 scatterers/mm$^2$, FIG. 7B is with 4 scatterers/mm$^2$, FIG. 7C is with 8 scatterers/mm$^2$, and FIG. 7D is with 16 scatterers/mm$^2$.

FIG. 9A-9D show the conventional B-mode and Nakagami images according to the present invention of the type-II phantom (No. 1), wherein FIG. 9A represents the conventional B-mode using gains of −10 dB, FIG. 9B represents the conventional B-mode using gains of 10 dB, FIG. 9C represents the Nakagami images according to the present invention using grayscale, and FIG. 9D represents the Nakagami images according to the present invention using pseudocolor.

FIG. 10A-10D show the conventional B-mode and Nakagami images according to the present invention of the type-II phantom (No. 2), wherein FIG. 10A represents the conventional B-mode using gains of −10 dB, FIG. 10B represents the conventional B-mode using gains of 10 dB, FIG. 10C represents the Nakagami images according to the present invention using grayscale, and FIG. 10D represents the Nakagami images according to the present invention using pseudocolor.

FIG. 11A-11D show the conventional B-mode and Nakagami images according to the present invention of the type-II phantom (No. 3), wherein FIG. 11A represents the conventional B-mode using gains of −10 dB, FIG. 11B represents the conventional B-mode using gains of 10 dB, FIG. 11C represents the Nakagami images according to the present invention using grayscale, and FIG. 11D represents the Nakagami images according to the present invention using pseudocolor.

DETAILED DESCRIPTION OF THE PREFERRED EMBODIMENTS

Figure 1:
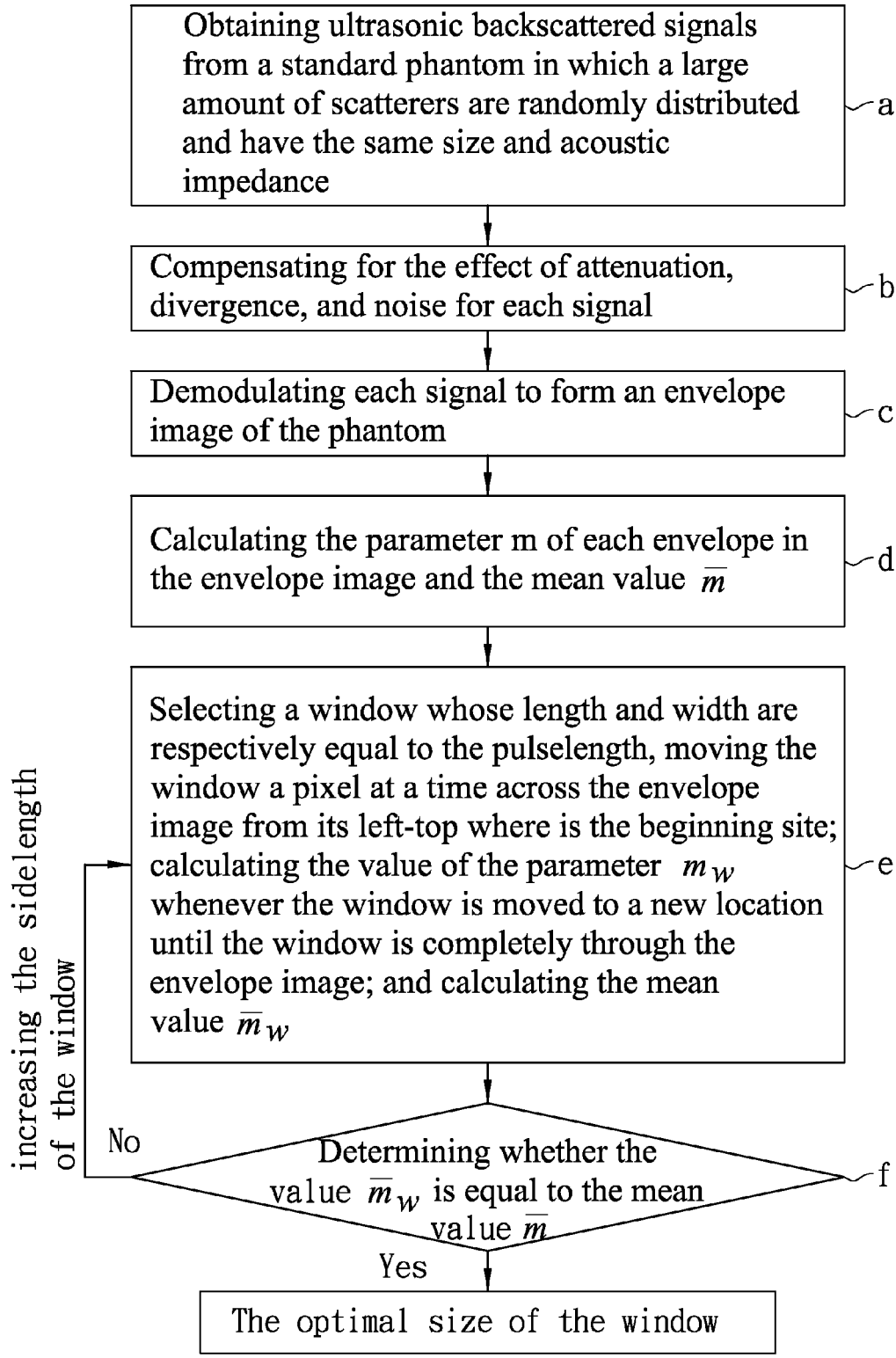
FIG. 1 shows a flow chart of a correcting procedure of the present invention.
Figure 2:
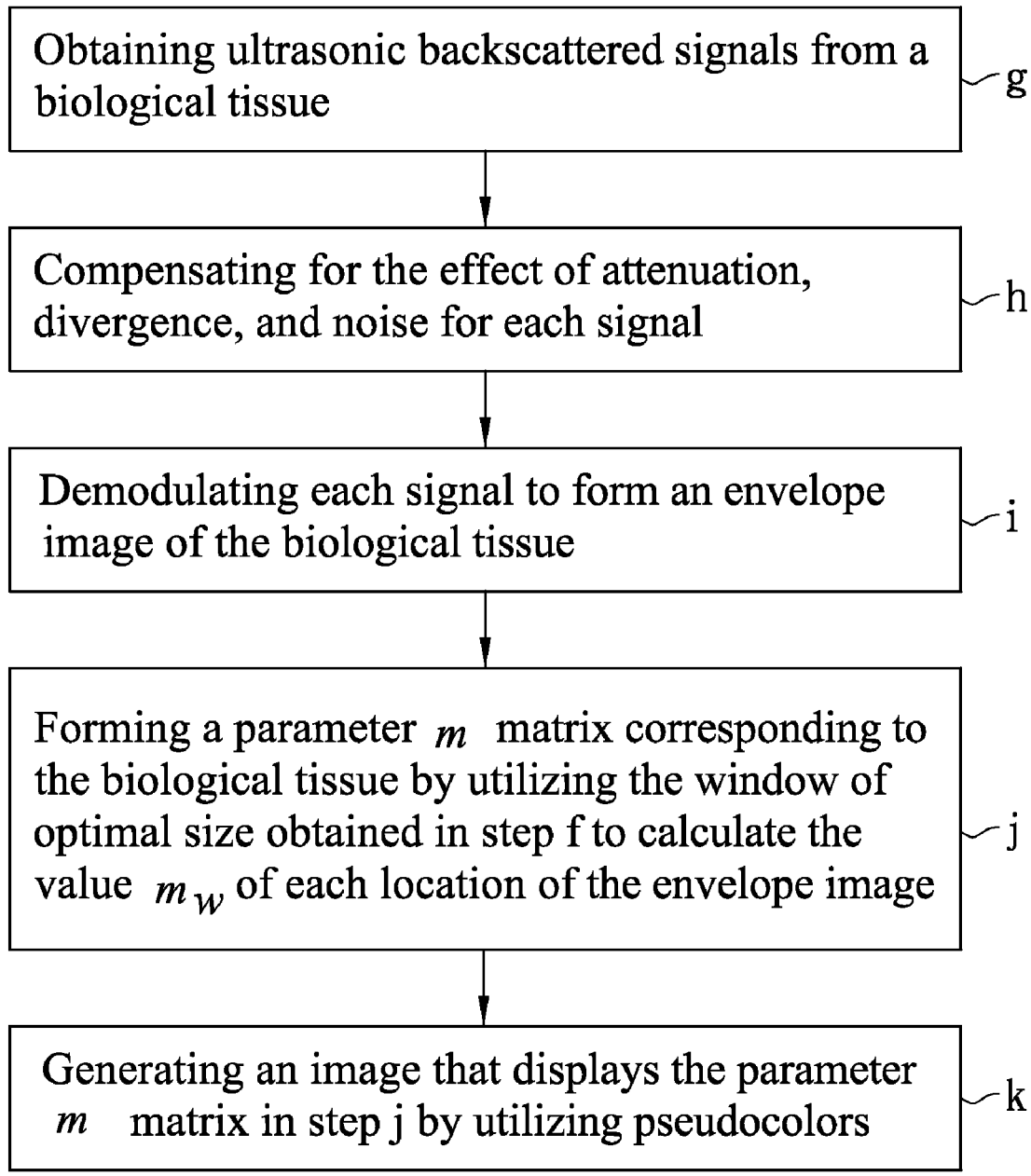
FIG. 2 shows a flow chart of an imaging procedure of the present invention.

FIGS. 1 and 2 show flow charts of a correcting procedure and an imaging procedure according to the present invention, wherein:

the correcting procedure comprises steps of:
a. obtaining ultrasonic backscattered signals from a standard phantom in which a large amount of scatterers are randomly distributed and have the same size and acoustic impedance;
b. compensating for the effect of attenuation, divergence, and noise for each signal;
c. demodulating each signal to form an envelope image of the phantom;
d. calculating the parameter m of each envelope in the envelope image and the mean value $\overline{m}$;
e. selecting a window whose length and width are respectively equal to the pulselength, moving the window a pixel at a time across the envelope image from its left-top where is the beginning site; calculating the value of the parameter $m_w$ whenever the window is moved to a new location until the window is completely through the envelope image; and calculating the mean value $\overline{m}_w$; and
f. determining whether the value $\overline{m}_w$ is equal to the mean value $\overline{m}$, if not, then increasing the length and width of the window and repeating the step e; and if $\overline{m}_w = \overline{m}$, the window has its optimal size; and the imaging procedure comprises steps of:
g. obtaining ultrasonic backscattered signals from a biological tissue
h. compensating for the effect of attenuation, divergence, and noise for each signal;
i. demodulating each signal to form an envelope image of the biological tissue;
j. forming a parameter m matrix corresponding to the biological tissue by utilizing the window of optimal size obtained in step f to calculate the value $m_w$ of each location of the envelope image; and
k. generating an image that displays the parameter m matrix in step j by utilizing pseudocolors.

Figure 3:
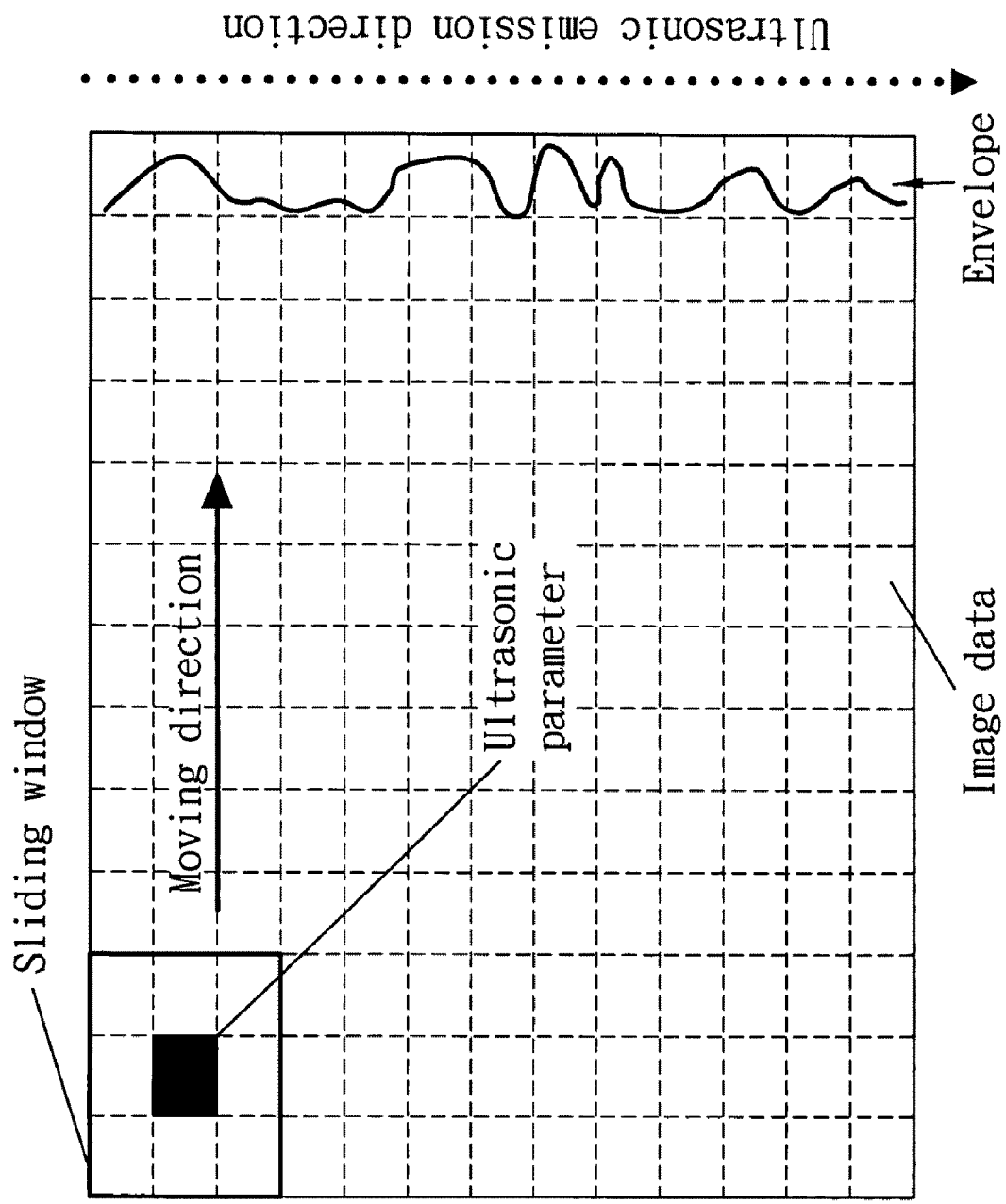
FIG. 3 is a schematic diagram showing a window moving on an envelope image according to the present invention.

FIG. 3 shows a window used in the correcting and imaging procedure moving on an envelope image according to the present invention. After the size of a window is determined, the window is moved from the top-left of the envelope image in a left-to-right and top-to-bottom direction. Whenever the window moved in a new location, a parameter value of that location is calculated.

In order to explain embodiments, we will introduce the relevant theoretical background of Nakagami distribution and demonstrate the embodiments via computer simulation in two-dimension.

The pdf (possibility density function) $f(r)$ of the ultrasonic backscattered envelope R under the Nakagami statistical model is given by $$f(r) = \frac{2m^m r^{2m-1}}{\Gamma(m)\Omega^m} \exp\left(-\frac{m}{\Omega} r^2\right) U(r),$$

where $\Gamma(\cdot)$ and $U(\cdot)$ are the gamma function and the unit step function, respectively. Let $E(\cdot)$ denote the statistical mean, the scaling parameter $\Omega$ and the Nakagami parameter m associated with the Nakagami distribution can be respectively obtained from $$\Omega = E(R^2)$$

and $$m = \frac{[E(R^2)]^2}{E[R^2 - E(R^2)]^2}.$$

The Nakagami parameter m is a shape parameter to determine the statistical distribution of the ultrasonic backscattered envelope. As the parameter m varies from 0 to 1, the statistics of the envelope changes from pre-Rayleigh to the Rayleigh distribution, and the backscattered statistics is post-Rayleigh distributions if m is larger than 1. Because different scatterer concentrations result in different envelope statistics, the parameter m is a good parameter for quantifying concentrations of scatterers in the tissues.

We apply the system-based model to simulate the ultrasonic backscattered echoes and the B-mode image of the biological tissue. Firstly, to reduce the computational complexity, the 3-D model is simplified to a simple model in two dimensions. The acoustic attenuation, beam diffraction, and system noise are not considered to achieve the ideal and undistorted shape of the ultrasonic backscattered signals. Subsequently, the computer phantoms with different scatterers concentrations are constructed, in which the sound velocity is 1540 m/s, and the internal scatterers are assumed to be randomly distributed point targets with the same relative echogenicity coefficient $c_r$. For the convenient discussion, we call these phantoms the type-I phantom. Then, a Gaussian incident wave with a central frequency of 5 MHz is generated, in which the −6 dB bandwidth is 4 MHz, and the pulselength and the −3 dB beamwidth are 0.9 mm and 0.5 mm, respectively. Consequently, the simulated ultrasonic backscattered signals (scan-lines for imaging) correspond to the convolution of the incident wave with the computer phantom. For each phantom of a specific scatterer concentration, an area consisted of totally 1000 image scan-lines corresponding to approximately 3×3 cm$^2$ is selected as the region of interest (ROI) for imaging and analysis. Each scan-line is demodulated to obtain the envelope image of the ROI, and the B-mode images of different system gains and dynamic ranges are formed from the logarithm-compressed envelope image.

The Nakagami parametric images for the phantoms of different scatterers concentrations are generated using the sliding window to process their envelope images. The sliding window technique is a typical method to form the ultrasonic parametric image and mainly contains two steps.

(1) A subimage, termed a window, within the envelope image of the ROI is chosen to collect the local backscattered envelopes for estimating the local Nakagami parameter $m_w$. The parameter $m_w$ is then assigned as the new pixel located in the center of the window.

(2) Let the window move throughout the whole envelope image in steps of one pixel, and repeat the step 1. Thus, the Nakagami image of the ROI can be constructed using the map of the parameter $m_w$.

Note that the window size determines the resolution of the ultrasonic parametric image. As the window size decreases, the resolution of the parametric image gets better. However, the small window has less numbers of the envelope data, leading to an unstable estimation of the parameter $m_w$. Therefore, prior to the construction of the Nakagami image, the optimal size of the window that can simultaneously satisfy both the stable estimation of $m_w$ and an acceptable resolution of the parametric image needed to be determined. The procedure we use to determine the optimal window size is described as follows.

(1) For the ROI, each envelope signal of the image scan-line is used to calculate the Nakagami parameter m and the average Nakagami parameter $\overline{m}$. Compared to the previous studies, a 3-cm-long envelope signal of the image scan-line in the ROI is certainly large enough to satisfy the stable estimation of m, and $\overline{m}$ can be treated as an indicator of the global backscattered statistics of the ROI.

(2) Each $m_w$ in the ROI and their average value $\overline{m}_w$ are subsequently estimated using different increasing sizes of the sliding window. Assuming that the window size is large enough (but no too large) to satisfy the stable estimation of the parameter $m_w$, the result of $\overline{m}_w$ should approaches that of $\overline{m}$ to reflect the identical global backscattered statistics of the ROI. Consequently, the optimal window size is determined once $\overline{m}_w = \overline{m}$.

After determination of the window size, the Nakagami images of those type-I phantoms are constructed. With the same simulation procedure and the same size of the sliding window, we further explore and compare the B-mode and the Nakagami-mode images of another three phantoms. In contrast to the type-I phantom, we classify these phantoms as the type-II phantom. They consist of a background material containing a cylinder object with a diameter of 1 cm and have different $c_r$ and scatterer concentrations in the background and in the embedded cylinder. The scatterer properties of these type-II phantoms are shown in Table 1 below.

TABLE 1

|  | Scatterer concentration in the background (mm$^{-2}$) | Scatterer concentration in the cylinder (mm$^{-2}$) | $C_{r(background)}:C_{r(cylinder)}$ |
|---|---|---|---|
| Phantom No. 1 | 16 | 16 | 5:1 |
| Phantom No. 2 | 16 | 6 | 1:5 |
| Phantom No. 3 | 6 | 16 | 5:1 |

In order to clearly reveal the information of the Nakagami parametric image, both the grayscale and pseudocolor are applied to display the Nakagami parameter map. The parameter $m_w$ smaller than 1 are assigned the blue shades varying from deep to shallow with the increasing parameter value, representing various pre-Rayleigh statistics of the backscattered envelope. When $m_w$ equal 1, the shade is white to express the Rayleigh distribution, and those larger than 1 are assigned the shades of progressive red color in accordance with the increasing parameter value, indicating the incremental degree of the post-Rayleigh distributions in the backscattered statistics.

The results obtained from the computer simulations will be divided into four parts for the discussion. The conventional B-mode images of the type-I phantoms with different scatterer concentrations will be discussed first. Then the optimal window size in the formation of the Nakagami image and the Nakagami images of the type-I phantoms according to the present invention are determined. Finally the conventional B-mode and Nakagami images according to the present invention of the three type-II phantoms (No. 1 to 3) are compared.

Part One: The B-Mode Images of the Type-I Phantom

Figure 4A:
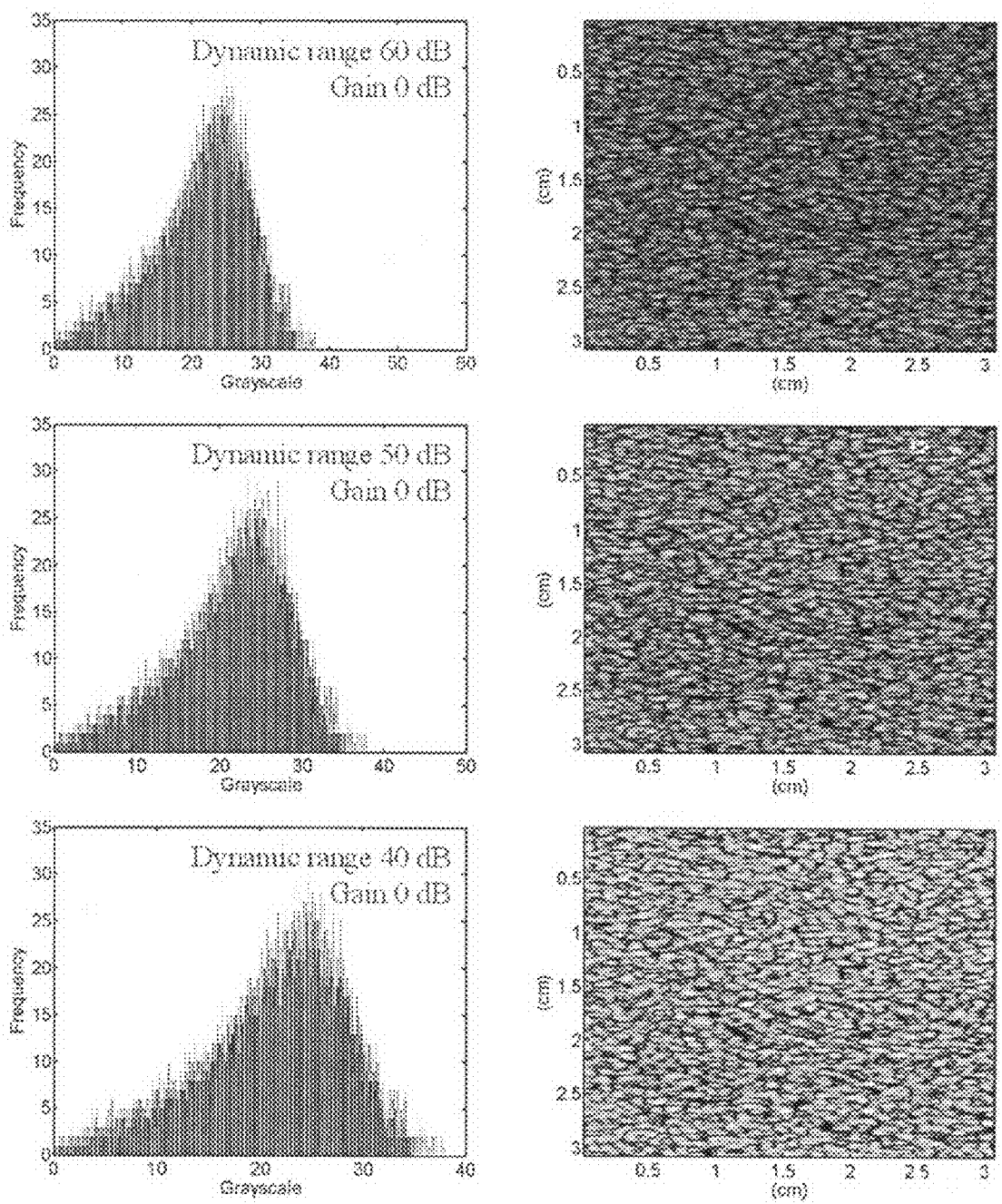
Figure 4B:
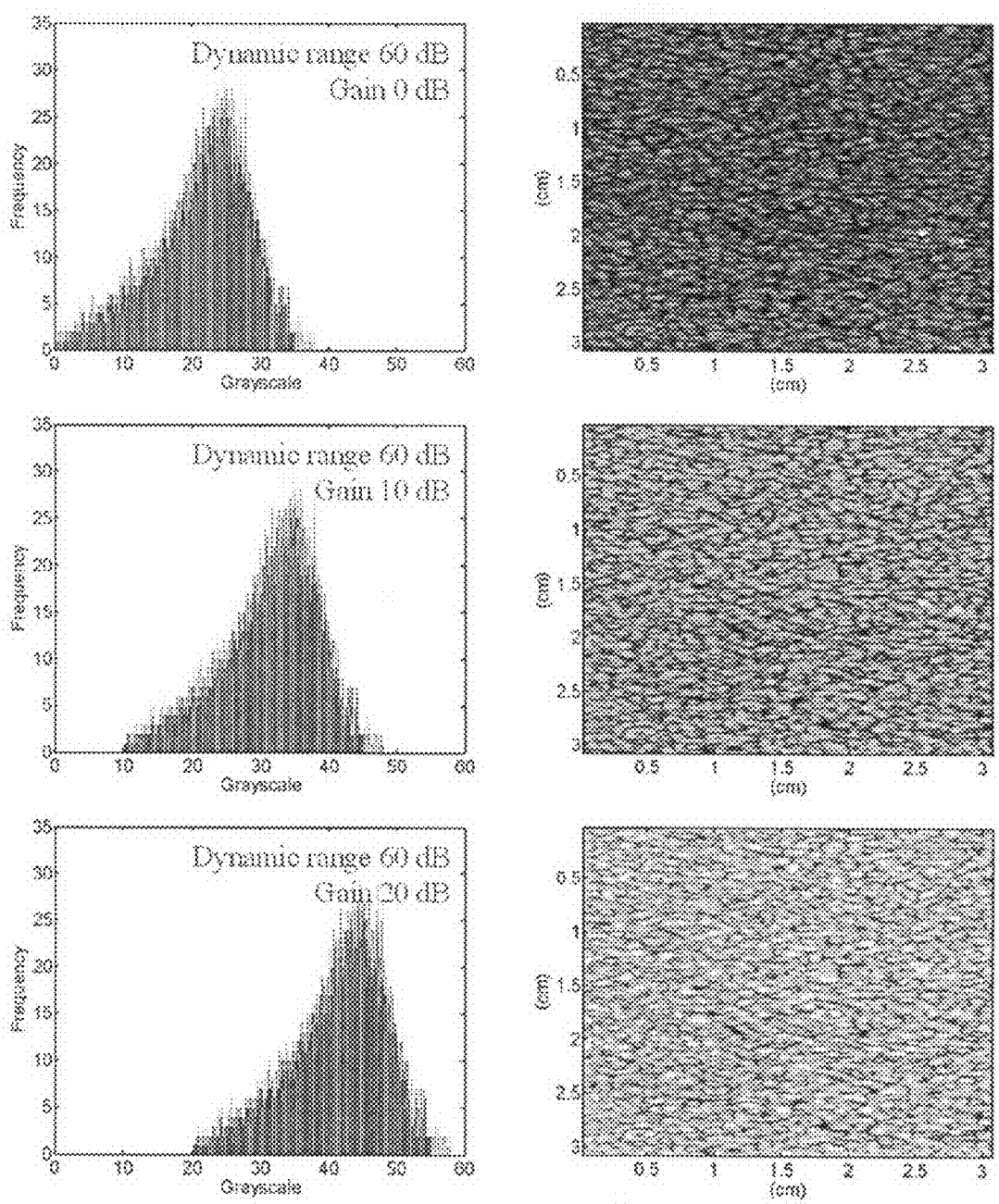

FIGS. 4A and 4B show the conventional B-mode image and its grayscale histogram for the type-I phantom of the scatterer concentration of 8 scatterers/mm$^2$, wherein FIG. 4A is with constant system gain and different dynamic ranges and FIG. 4B is with constant dynamic range and different system gains. The histogram of the image grayscale broadens with decreasing the dynamic range of the B-mode image from 60 to 40 dB when the system gain is constant. This enhances the image contrast without changing the mean echo amplitude. If we fix the dynamic range at 60 dB as the system gain is increased from 0 to 20 dB, the histogram of the image grayscale maintains the same width and shape but shifts towards the right side, increasing the overall brightness of the B-mode image but not altering the image contrast. Hence, the brightness and the contrast of the B-mode image strongly depend on the dynamic range and the system gain, implying that the B-mode images measured by different diagnosticians using different ultrasonic systems for the same examined tissue may be different.

Figure 5A:
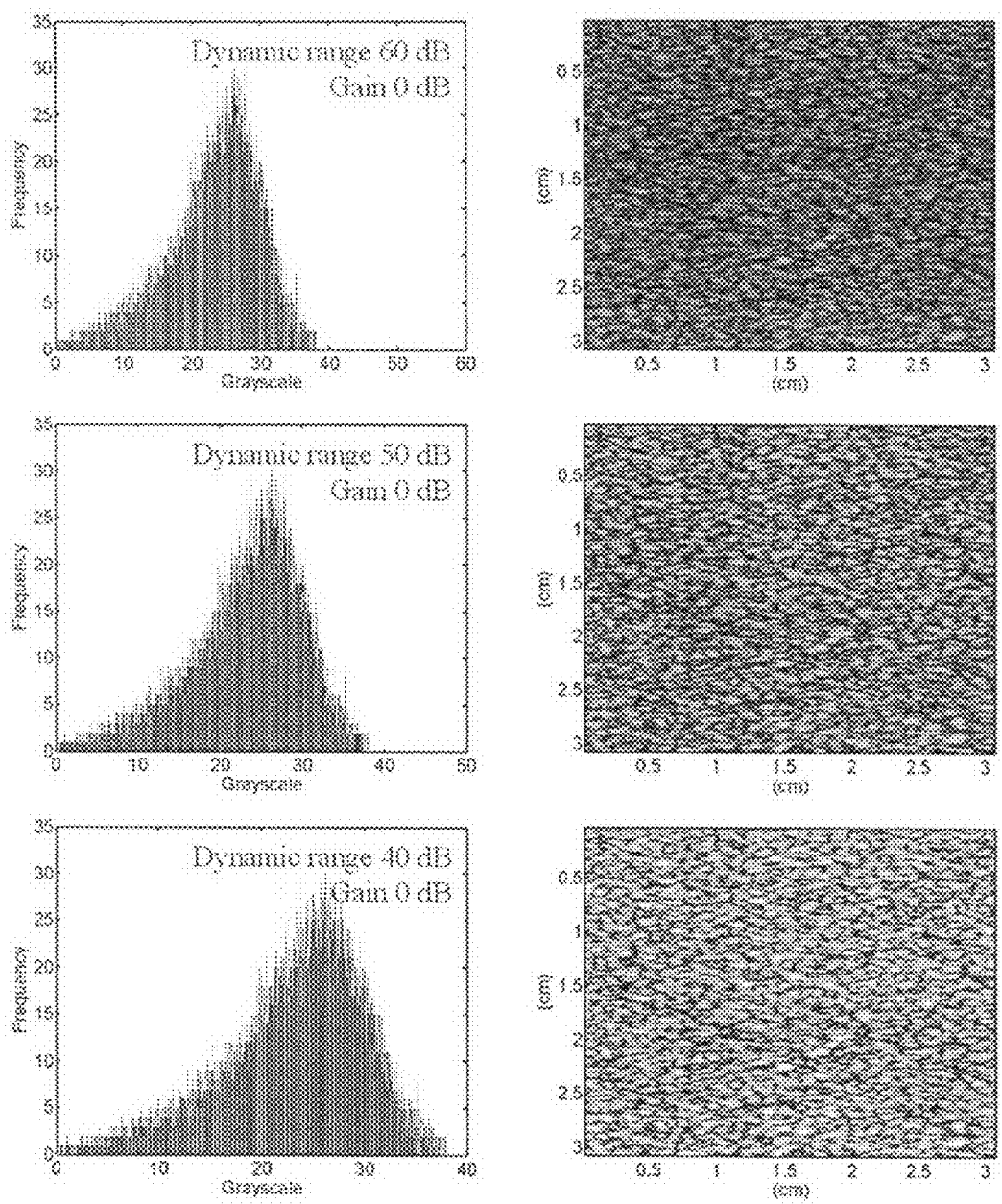
Figure 5B:
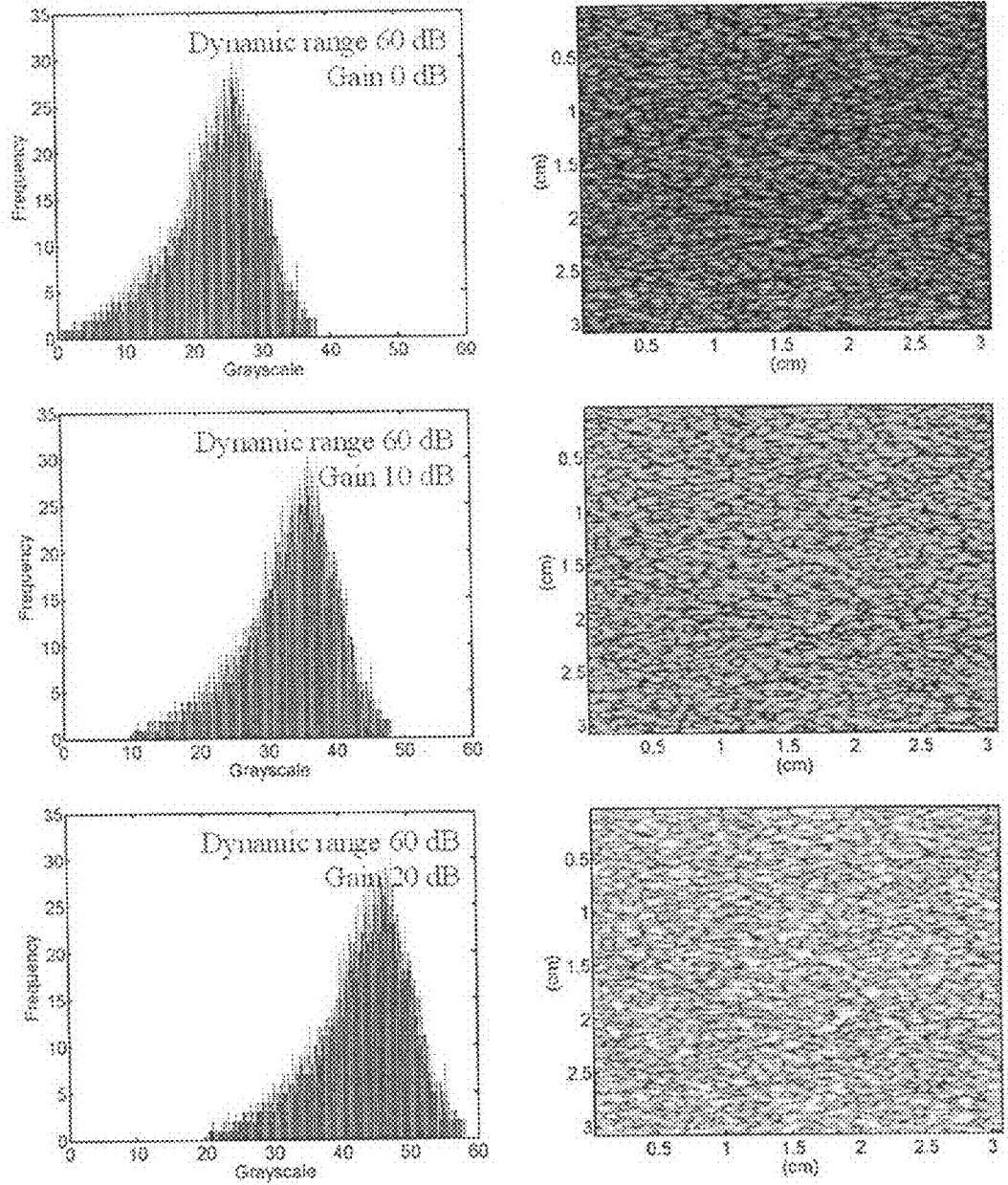

FIGS. 5A and 5B show the conventional B-mode image and its grayscale histogram for the type-I phantom of the scatterer concentration of 16 scatterers/mm$^2$, wherein FIG. 5A is with constant system gain and different dynamic ranges and FIG. 5B is with constant dynamic range and different system gains. The result indicates that the conventional B-mode images are not consistent when different operation settings are used. Moreover, comparison of FIG. 4A-4B with FIG. 5A-5B shows that the B-mode images with various scatterer concentrations would become similar to each other under certain dynamic ranges and gains, resulting in that the scatterer properties in a biological tissue cannot be identified in the conventional grayscale image. These results and previous studies demonstrate that the tissue properties are difficult to obtain from the B-scans.

Part Two: The Optimal Window Size Used to Form the Nakagami Image

Figure 6:
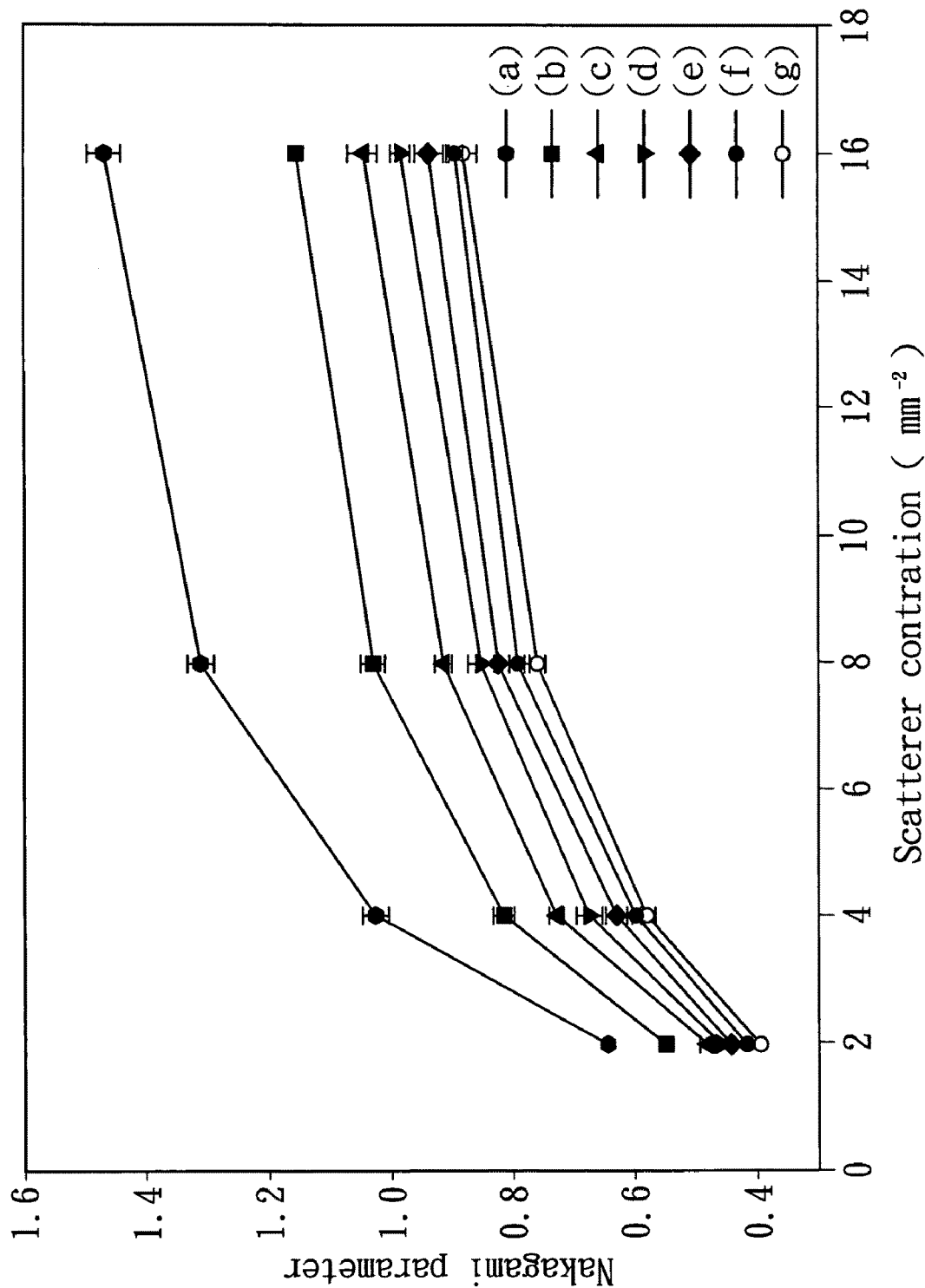
FIG. 6 shows the curves a-f of $\overline{m}_w$ as a function of scatterer concentration estimated using different window sizes and the curve of $\overline{m}$ as a function of scatterer concentration estimated from the envelope signal of the image scan-line.

To visualize the scatterer properties of the phantom, the Nakagami parametric images of different scatterer concentrations are constructed. Before this, the optimal size of the sliding window used to form the Nakagami parametric image has to be determined. FIG. 6 shows the curves a-f of $\overline{m}_w$ as a function of scatterer concentration estimated using different window sizes and the curve of $\overline{m}$ as a function of scatterer concentration estimated from the envelope signal of the image scan-line, wherein curve a represents the window size of 0.9×0.9 mm$^2$, curve b represents the window size of 1.35×1.35 mm$^2$, curve c represents the window size of 1.8×1.8 mm$^2$, curve d represents the window size of 2.25×2.25 mm$^2$, curve e represents the window size of 2.75×2.7 mm$^2$, and curve f represents the window size of 3.15×3.15 mm$^2$. The parameter $\overline{m}$ is increased from 0.41 to 0.91 with increasing the scatterer concentration from 2 to 16 scatterers/mm$^2$. This result agrees well with those in the previous studies, indicating that the global pdf of the backscattered envelope would change from the pre-Rayleigh to Rayleigh statistics with increasing the scatterer concentration. Note that, with increasing the window size, the curve of $\overline{m}_w$ as the scatterer concentration gradually approaches that of $\overline{m}$. It is found that the parameter $\overline{m}_w$ is increased from about 0.42 to 0.93 with increasing the scatterer concentration from 2 to 16 scatterers/mm$^2$ when the window size is 2.7×2.7 mm$^2$. This demonstrates that an appropriate size of the window can satisfy the stable estimation of the parameter $m_w$, enabling the average of the local Nakagami parameters $\overline{m}_w$ to represent the correct global backscattered statistics, as assumed in the section of methods. More precisely, this result further implies that the size of the window corresponding to the square with the sidelength equal to 3 times the pulselength may be an optimal size for the stable estimation of $m_w$ (because 2.7 mm is about 3 times the pulselength). On the other hand, the window size cannot be too large, as we could take $m_w$ to distinguish the variation of the local scatterer concentration. Accordingly, the window size of 2.7×2.7 mm$^2$ is applied in the following constructions of the Nakagami image.

Part Three: The Nakagami Images of the Type-I Phantom

FIG. 7A-7D show Nakagami parametric images according to the present invention with a grayscale display for the type-I phantoms of various scatterer concentrations, wherein FIG. 7A is with 2 scatterers/mm$^2$, FIG. 7B is with 4 scatterers/mm$^2$, FIG. 7C is with 8 scatterers/mm$^2$, and FIG. 7D is with 16 scatterers/mm$^2$. The overall brightness of the Nakagami image is increased with increasing the scatterer concentration from 2 to 16 scatterers/mm$^2$, because the global backscattered statistics varied from the pre-Rayleigh to Rayleigh distribution with increasing the scatterer concentration make $\overline{m}_w$ increase. However, the brightness in each local region in the Nakagami image is different for each phantom due to the fact that each local region has different values of $m_w$. Namely, we have formed the Nakagami image with $m_w$. The Nakagami image can be applied to the detection of the local scatterer aggregation in a tissue. Furthermore, compared with the B-mode image, the Nakagami image is relatively robust in producing a consistent image for different users, imaging systems, and operation settings. The reason for the consistent image lies in the fact that the pixel of the Nakagami image is $m_w$, which is only dependent on the shape of the local envelope statistics and not affected by the magnitude of the local envelope signal.

FIG. 8A-8D show the Nakagami parametric images according to the present invention with a pseudocolor display for the type-I phantoms of various scatterer concentrations, wherein FIG. 7A is with 2 scatterers/mm$^2$, FIG. 7B is with 4 scatterers/mm$^2$, FIG. 7C is with 8 scatterers/mm$^2$, and FIG. 7D is with 16 scatterers/mm$^2$. The results show that the Nakagami images can more directly and conveniently visualize the scatterer properties of the biological tissues. It is found that the Nakagami images of the phantoms with relatively low scatterer concentrations have more blue shades and less red regions. This represents that the low scatterer concentration would cause a larger spacing between the scatterers in a medium, rendering the most statistics of the local backscattered envelope to be the pre-Rayleigh distributions. On the other hand, the red region spread with increasing the scatterer concentration. It means that the high scatterer concentration result in a comparatively small spacing between the scatterers in a medium, leading to a conspicuous effect of the scatterer aggregation and that the most of the local envelope signals tend to be the post-Rayleigh distribution.

Part Four: The B-Mode and Nakagami-Mode Images of the Type-II Phantom

To further evaluate the performance of the Nakagami parametric image in characterizing the biological tissues, three type-II phantoms are simulated to compare their B-mode and Nakagami images.

Figure 9A:
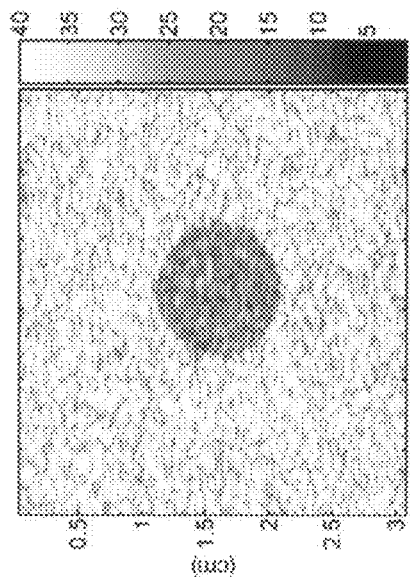
Figure 9B:
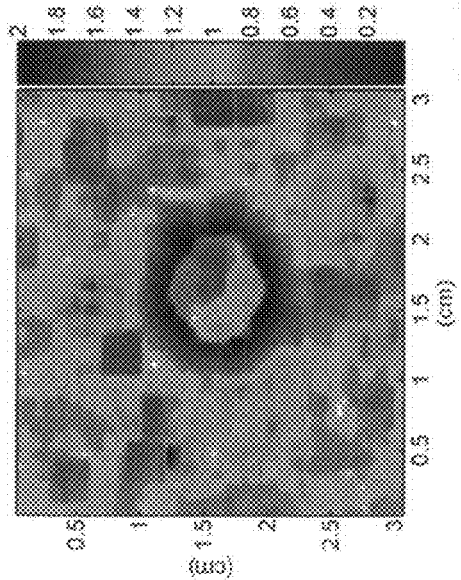
Figure 9C:
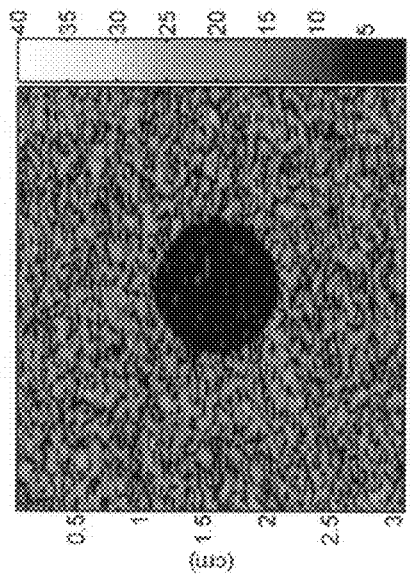
Figure 9D:
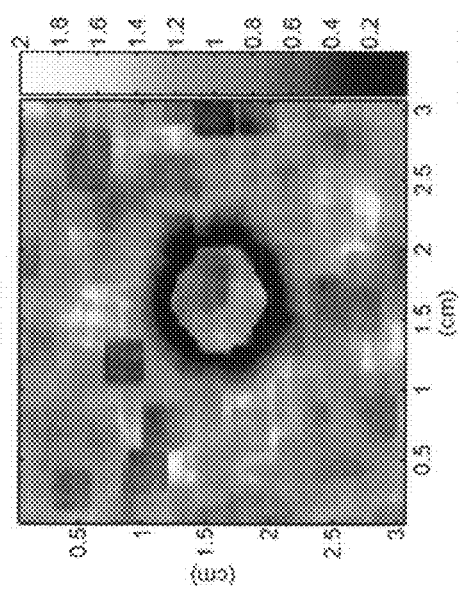

FIG. 9A-9D show the conventional B-mode and Nakagami images according to the present invention of the type-II phantom (No. 1), wherein FIG. 9A represents the conventional B-mode using gains of −10 dB, FIG. 9B represents the conventional B-mode using gains of 10 dB, FIG. 9C represents the Nakagami images according to the present invention using grayscale, and FIG. 9D represents the Nakagami images according to the present invention using pseudocolor. Due to the scatterer echogenicity coefficient in the background is 5-fold of that in the cylinder, the scatterers in the cylinder are relatively weak scatterers, leading to the weak backscattered signals and darker brightness of the B-mode image. Note that the cylinder in the B-mode image behaves as an area without any returned echoes when the system gain is low. This may easily mislead the diagnosticians with less experience in describing the properties of the scatterers in the cylinder. Instead, the Nakagami image clearly indicates that the cylinder is not an empty region.

FIG. 10A-10D show the conventional B-mode and Nakagami images according to the present invention of the type-II phantom (No. 2), wherein FIG. 10A represents the conventional B-mode using gains of −10 dB, FIG. 10B represents the conventional B-mode using gains of 10 dB, FIG. 10C represents the Nakagami images according to the present invention using grayscale, and FIG. 10D represents the Nakagami images according to the present invention using pseudocolor. The scatterer properties for the phantom No. 2 enable the B-mode image of the cylinder region to be brighter. This may produces a problem that the diagnosticians would treat the cylinder object as a high scatterer concentration area. In the meantime, the Nakagami image indicates that the scatterer concentration of the cylinder is actually lower than the background.

FIG. 11A-11D show the conventional B-mode and Nakagami images according to the present invention of the type-II phantom (No. 3), wherein FIG. 11A represents the conventional B-mode using gains of −10 dB, FIG. 11B represents the conventional B-mode using gains of 10 dB, FIG. 11C represents the Nakagami images according to the present invention using grayscale, and FIG. 11D represents the Nakagami images according to the present invention using pseudocolor. The scatterer properties of the phantom No. 3 make the B-mode image in the cylinder darker. As a result, we cannot tell that the scatterer concentration of the cylinder is higher than that of the background using the B-mode image. On the contrary, the Nakagami image can successfully indicate that the cylinder region has a higher scatterer concentration than the background.

In summary, the comparisons of the Nakagami image with the conventional B-scans are listed in the Table 2 below.

TABLE 2

|  | B-mode image | Nakagami image |
| --- | --- | --- |
| Image pixel | Grayscale | Local Nakagami parameter |
| Image physical meaning | Relative echo intensity | Envelope statistics |
| Image type | Qualitative | Quantitative |
| Resolution | Relatively Better | Relatively poor |
| Medical application | Morphology analysis | Scatterer concentration differentiation |

We consider that the B-mode image and the Nakagami image are complementary to each other. The B-mode image is responsible for the morphology analysis, and the Nakagami image is used to evaluate the distribution of the scatterers in the tissue.

In this study, we have explored the ultrasonic parametric image based on the map of the Nakagami parameter. In particular, the computer simulations have been carried out to generate phantoms of various scatterer properties for comparing the B-mode and Nakagami-mode images to evaluate their individual performance in the ultrasonic tissue characterization. According to the simulated results, the optimal size of the sliding window used to construct the Nakagami image is the square with the sidelength equal to three times the pulselength of the incident ultrasound. The Nakagami image constructed using this window size can provide both the global and local backscattered statistics of the ultrasonic signals in a tissue, demonstrating that the Nakagami image has an outstanding ability to detect the local scatterer concentrations in a tissue. Moreover, compared to the B-mode image that is easily influenced by the factors related to the system and operator, the Nakagami image yields a comparatively consistent image result for different dynamic ranges and system gains. This is because the Nakagami image formation is based on the shape of the local backscattered envelope in the tissue and would not be affected by the magnitude of the ultrasonic backscattered signal. Furthermore, this imaging principle associated with the Nakagami image enables extraction of the weak backscattering information that may be lost in the B-mode image. For these reasons, the Nakagami image has a great potential to become a new diagnostic tool, which is easily combined with the use of the conventional B-scans to simultaneously visualize the structures and the scatterer properties in the tissue. Nevertheless, experimental and clinical validations must be carried out before the local scatterer concentration image based on the Nakagami model can be used as a reliably clinical or research tool.

Accordingly, as disclosed in the above description and attached drawings, the present invention can provide an ultrasonic imaging technique for differentiating the distribution of scatterers within a tissue, which will not be affected by system settings and user operations, can evaluate the concentration and arrangement of scatterers in a biological tissue, and can differentiate the distribution of scatterers within a tissue for assisting the use of a B-mode ultrasonic image. It is new and can be put into industrial use.

While the invention has been described with reference to certain embodiments, it will be understood by those skilled in the art that various changes may be made and equivalents may be substituted without departing from the scope of the present invention.

What is claimed is:

1. An ultrasonic imaging technique for differentiating the distribution of scatterers within a tissue by utilizing Nakagami parameter m, comprising a correcting and an imaging procedure, wherein the correcting procedure comprises steps of:
- a. obtaining ultrasonic backscattered signals from a standard phantom in which a large amount of scatterers are randomly distributed and have a same size and acoustic impedance;
- b. compensating for the effect of attenuation, divergence, and noise for each signal;
- c. demodulating each signal to form an envelope image of the phantom;
- d. calculating the parameter m of each envelope in the envelope image and the mean value $\overline{m}$;
- e. selecting a window whose length and width are respectively equal to the pulselength, moving the window a pixel at a time across the envelope image from its left-top which is the beginning site calculating the value of the parameter $m_w$ whenever the window is moved to a new location until the window is completely through the envelope image; and calculating the mean value $\overline{m}_w$; and
- f. determining whether the value $\overline{m}_w$ is equal to the mean value $\overline{m}$, if not, then increasing the length and width of the window and repeating the step e, and if $\overline{m}_w = \overline{m}$, the window has its optimal size; and the imaging procedure comprises steps of:
- g. obtaining ultrasonic backscattered signals from a biological tissue;
- h. compensating for the effect of attenuation, divergence, and noise for each signal;
- i. demodulating each signal to form an envelope image of the biological tissue;
- j. forming a parameter m matrix corresponding to the biological tissue by utilizing the window of optimal size obtained in step f to calculate the value $m_w$ of each location of the envelope image; and
- k. generating an image that displays the parameter m matrix in step j by utilizing pseudocolors.

2. The imaging technique for differentiating the distribution of scatterers within a tissue as claimed in claim 1, wherein the value of parameter $m_w$ smaller than 1 is assigned one corresponding color shade, the value of parameter $m_w$ equal to 1 is assigned another color shade, and the value of parameter $m_w$ larger than 1 is assigned still another color shade.

* * * * *